United States Patent [19]

Bruns et al.

[11] 4,302,363
[45] Nov. 24, 1981

[54] PERFUME COMPOSITIONS CONTAINING 4(5)-ACETYL-7,7,9(7,9,9)-TRIMETHYLBICYCLO[4.3.0]NON-1-ENE

[75] Inventors: Klaus Bruns, Krefeld-Traar; Ursula Weber, Wachtendonk, both of Fed. Rep. of Germany

[73] Assignee: Henkel Kommanditgesellschaft auf Aktien, Düsseldorf-Holthausen, Fed. Rep. of Germany

[21] Appl. No.: 157,528

[22] Filed: Jun. 9, 1980

[30] Foreign Application Priority Data

Jun. 25, 1979 [DE] Fed. Rep. of Germany ....... 2925622

[51] Int. Cl.³ .............................................. A61K 7/46
[52] U.S. Cl. ............................ 252/522 R; 568/374; 568/343
[58] Field of Search ................... 252/522 R; 568/374

[56] References Cited

U.S. PATENT DOCUMENTS 3,681,464  8/1972  Theimer ........................... 252/522 R
4,206,089  6/1980  Willis et al. ...................... 252/522 R

OTHER PUBLICATIONS

Arctander *Perfume and Flavor Chemicals*, vol. 1, No. 40, (1969).

*Primary Examiner*—John F. Niebling
*Attorney, Agent, or Firm*—Hammond & Littell, Weissenberger and Muserlian

[57] ABSTRACT

This invention is directed to the isomer mixture 4(5)-acetyl-7,7,9(7,9,9)-trimethylbicyclo[4.3.0]non-1-ene, the preparation thereof, and the use of said mixture as a perfuming agent. The isomer mixture represents a valuable new perfuming agent having strong, warm ambergris scent with woody tobacco leaf, methyl ionone, and arborvitae notes and having exceptional persistence as well.

5 Claims, No Drawings

PERFUME COMPOSITIONS CONTAINING 4(5)-ACETYL-7,7,9(7,9,9)-TRIMETHYLBICYCLO[4.3.0]NON-1-ENE

FIELD OF THE INVENTION

This invention relates to the preparation of a novel mixture of isomers and its use. More particularly, this invention relates to a mixture of substituted bicyclo nonenes, the preparation thereof, and the use of such a mixture as a perfuming agent.

OBJECTS OF THE INVENTION

It is an object of this invention to provide a method of preparing the isomer mixture 4(5)-acetyl-7,7,9(7,9,9)-trimethylbicyclo[4.3.0]non-1-ene.

It is also an object of this invention to provide a method of using said isomer mixture as a perfuming agent.

It is a further object of this invention to provide perfuming agents and perfume compositions having characteristic fragrances and excellent adhesion.

It is a yet further object of this invention to provide perfuming agents and perfumery compositions comprising the isomer mixture 4(5)-acetyl-7,7,9(7,9,9)-trimethylbicyclo[4.3.0]-non-1-ene.

These and other objects of the invention will become more apparent in the discussion below.

DETAILED DESCRIPTION OF THE INVENTION

It has been found that the isomer mixture 4(5)-acetyl-7,7,9(7,9,9)-trimethylbicyclo[4.3.0]non-1-ene represents a strong, warm ambergris scent with woody tobacco leaf, methyl ionone, and arborvitae notes and having exceptional persistance. The novel isomer mixture according to the invention is prepared by well-known syntheses of organic chemistry, which proceed according to the following reaction scheme:

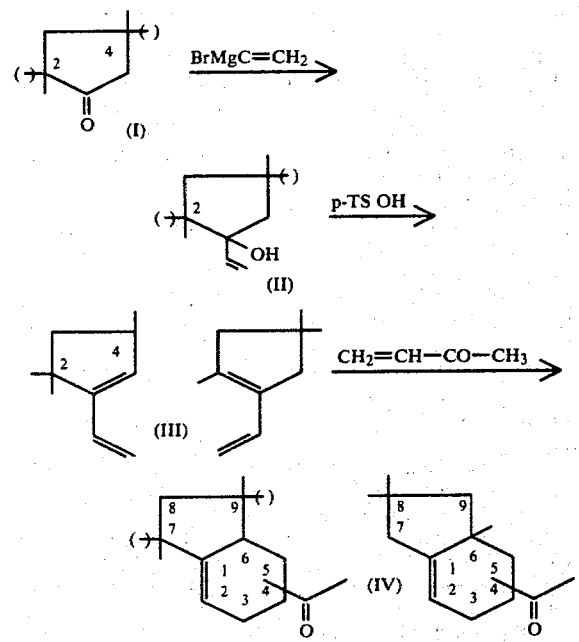

wherein Formula I represents a mixture of the isomers 2,2,4-trimethylcyclopentanone and 2,4,4-trimethylcyclopentanone, i.e., 2,2,4(2,4,4)-trimethylcyclopentanone, which is converted via the Grignard reaction into Formula II, which represents a mixture of the isomers 1-vinyl-1-hydroxy-2,2,4-trimethylcyclopentane and 1-vinyl-1-hydroxy-2,4,4-trimethylcyclopentane, i.e., 1-vinyl-1-hydroxy-2,2,4(2,4,4)-trimethylcyclopentane.

The trimethylcyclopentanone used as starting material is always in the form of the isomer mixture I, and it is not possible to separate the isomers to provide isolated, structurally uniform compounds.

The isomer mixture II is dehydrated in the presence of p-toluene sulfonic acid to provide a mixture of the isomers 1-vinyl-2,2,4-trimethylcyclopent-1-ene and 1-vinyl-2,4,4-trimethylcyclopent-1-ene, i.e., 1-vinyl-2,2,4(2,4,4)-trimethylcyclopent-1-ene, represented by the Formula III. The Formula III mixture is converted into the desired isomer mixture 4(5)-acetyl-7,7,9-(7,9,9)-trimethylbicyclo[4.3.0]non-1-ene IV by means of a Diels-Alder reaction with methylvinyl ketone.

The isomer mixture IV is a position/stereoisomer mixture with respect to the carbon atoms in the 4, 5, 6, 7, and 9 positions. Therefore, the perfuming agent of the invention comprises a mixture of the following isomers:

(i) 4-acetyl-7,7,9-trimethylbicyclo[4.3.0]non-1-ene
(ii) 5-acetyl-7,7,9-trimethylbicyclo[4.3.0]non-1-ene
(iii) 4-acetyl-7,9,9-trimethylbicyclo[4.3.0]non-1-ene
(iv) 5-acetyl-7,9,9-trimethylbicyclo[4.3.0]non-1-ene in which the acetyl group and the ring closure $C_6/C_7$ can have axial and equatorial configuration.

The isomer mixture 4(5)-acetyl-7,7,9(7,9,9)-trimethylbicyclo[4.3.0]non-1-ene is a valuable perfuming agent having a characteristic aroma, namely, a strong, warm ambergris scent with woody tobacco leaf, methyl ionone, and arborvitae notes, and is particularly suitable for the development of novel perfume compositions. The isomer mixture, which has exceptional persistance, can be easily combined into new and interesting fragrances to which it imparts its special persistance.

The isomer mixture 4(5)-acetyl-7,7,9(7,9,9)-trimethylbicyclo[4.3.0]non-1-ene to be used according to the invention can be mixed with other perfumes in various quantitative ratios to form new perfume compositions. In general, the isomer mixture in the perfume composition will comprise from about 1 to 50 percent by weight, based on the total weight of the perfuming composition. The remainder of the composition is comprised of conventional perfumery constituents. Perfume compositions of this type can be used directly as a perfume or, alternatively, for perfuming cosmetics, such as creams, lotions, toilet waters, aerosols, mouthwashes, and toilet soaps, as well as in perfume extracts. They can also be used to improve the odor of technical products, such as detergents, cleansers, fabric softeners, textile finishing agents, and the like. The perfuming compositions generally are added in concentrations of from about 0.05 to 2 percent by weight, based on the weight of the total product, for the perfuming of the various products.

The following examples are intended to explain further the subject of the invention, but without limiting the invention to these examples.

EXAMPLES

EXAMPLE I

Preparation of 4(5)-acetyl-7,7,9(7,9,9)-trimethylbicyclo[4.3.0]non-1-ene (a) Preparation of 1-vinyl-1-hydroxy-2,2,4(2,4,4)-trimethylcyclopentane.

An appropriate Grignard solution was prepared in the usual manner from 1.4 mols of magnesium and 1.4 mols of vinylbromide in 450 ml of anhydrous tetrahydrofuran. A solution of 1.3 mols of 2,2,4(2,4,4)-trimethylcyclopentanone (weight ratio of 2,2,4-trimethylcyclopentanone to 2,4,4-trimethylcyclopentanone in the mixture of 65:35) in 160 ml of tetrahydrofuran was added dropwise and with agitation. The mixture was then refluxed for 12 hours. After cooling, the reaction mixture was decomposed with a 10% solution of sulfuric acid and worked up in known manner. The solvent was removed by distillation and the reaction product was distilled under water jet vacuum. The reaction product obtained was a colorless liquid with the following analytical data:

Boiling Point (0.02 bar): 65°–71° C.

IR (film): 3460/cm (OH); 3085, 1640, 1412, 995, 191/cm (—CH=CH$_2$)

(b) Preparation of 1-vinyl-2,2,4(2,4,4)-trimethylcyclopent-1-ene.

An amount of 0.1 mol of 1-vinyl-1-hydroxy-2,2,4(2,4,4)-trimethylcyclopentane in 30 ml of chloroform was refluxed with water separation for 15 minutes, in the presence of 0.002 mol of p-toluene sulfonic acid. Next, 1 gm of sodium carbonate was added, and then the solvent was distilled off. The residue was taken up in ether, extracted with 2 N sodium hydroxide solution, and washed neutral with water. After removal of the solvent by distillation, the product was distilled under water jet vacuum. The reaction product was a colorless liquid with the following analytical data:

Boiling point (0.12 bar): 78°–84° C.

IR (film): 3080, 1635, 1415, 985, 893/cm (—CH=CH$_2$); 1588/cm (conjugation), 852, 840/cm (>C=CH—)

(c) Preparation of 4(5)-acetyl-7,7,9(7,9,9)-trimethylbicyclo[4.3.0]non-1-ene.

An amount of 1.1 mols of 1-vinyl-2,2,4(2,4,4)-trimethylcyclopent-1-ene and 1.2 mols of methylvinyl ketone were refluxed with agitation for three hours. The crude product obtained was distilled fractionally under vacuum produced with an oil pump. The isomer mixture of 4(5)-acetyl-7,7,9(7,9,9)-trimethylbicyclo[4.3.0]non-1-ene obtained in this manner had the following analytical data:

Boiling point (0.002 bar): 94°–103° C.

IR (film): 1710/cm (ketone); 1155/cm (—COCH$_3$)
$^1$H-NMR(CDCl$_3$): 0.76–1.08 ppm (m, 9H) (C—CH$_3$); 2.16 ppm (m, 3H) (CO—CH$_3$): 5.34 ppm (1H, m) (C=CH)

The product had a strong, warm ambergris scent with woody tobacco leaf, methyl ionone, and arborvitae notes.

The following represent examples of perfume compositions according to the invention:

EXAMPLE II

Fragrance Composition, Tobacco Base:

| Component | Parts by Weight |
|---|---|
| 4(5)-Acetyl-7,7,9(7,9,9)-trimethylbicyclo[4.3.0] non-1-ene | 300 |
| Geraniol | 120 |
| Vetiverol | 100 |
| Cedryl acetate | 50 |
| Cedarwood oil | 50 |
| Sandalwood oil | 50 |
| Oak moss resin | 40 |
| Guaiyl acetate | 30 |
| Gamma-methyl ionone | 30 |
| Benzophenone | 30 |
| Galaxolide | 30 |
| Patchouly oil | 30 |
| Olibanum oil | 25 |
| Isobutyl salicylate | 25 |
| Bergamot oil | 20 |
| Lavender oil | 20 |
| Methyl naphthyl ketone | 20 |
| Coumarin | 20 |
| Cinnamyl acetate | 10 |
| | 1,000 |

EXAMPLE III

Chypre Composition

| Component | Parts by Weight |
|---|---|
| 4(5)-Acetyl-7,7,9(7,9,9,)-trimethylbicyclo[4.3.0.]-non-1-ene | 200 |
| Orange oil, Florida | 280 |
| Bergamot oil | 200 |
| Jasmine, absolute | 50 |
| Vetiveryl acetate | 40 |
| Coumarin | 30 |
| Oak moss, absolute | 30 |
| Sandalwood oil, East Indies | 30 |
| Ketone musk | 30 |
| Patchouly oil | 30 |
| Labdanum resin | 20 |
| Vetiver oil | 20 |
| Ambroxan ®, available from HENKEL KGaA | 20 |
| Basil oil | 5 |
| Tarragon oil | 5 |
| Vanillin | 5 |
| Civet, absolute | 2 |
| Methylnonyl acetaldehyde, 10% solution | 2 |
| Undecylene aldehyde | 1 |
| | 1,000 |

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A perfume composition comprising an effective amount of a mixture of the stereoisomers of 4-acetyl-7,7,9-trimethylbicyclo[4.3.0]non-1-ene, 5-acetyl-7,7,9-trimethylbicyclo[4.3.0]non-1-ene, 4-acetyl-7,9,9-trimethylbicyclo[4.3.0]non-1-ene, and 5-acetyl-7,9,9-trimethylbicyclo[4.3.0]non-1-ene.

2. The perfume composition of claim 1 which comprises from about 1 to 50 percent by weight of said isomer mixture, the remainder comprising customary constituents of perfume compositions.

3. The perfume composition of claim 2 wherein said customary constituents of perfumery composition include at least one other perfume.

4. The method of imparting a desired aroma to a product which comprises administering an aroma-imparting amount of the perfume composition of claim 1.

5. The method of claim 4 wherein from about 0.05 to 2 percent by weight of the perfume composition is administered.